(12) United States Patent
Kurtz et al.

(10) Patent No.: US 8,437,976 B2
(45) Date of Patent: May 7, 2013

(54) GAS DENSITY TRANSDUCER WITH A MICROPROCESSOR EXECUTING AN ALGORITHM SOLVING VAN DER WAAL'S EQUATION

(75) Inventors: Anthony D. Kurtz, Saddle River, NJ (US); Wolf S. Landmann, Fair Lawn, NJ (US)

(73) Assignee: Kulite Semiconductor Products, Inc., Leonia, NJ (US)

(*) Notice: Subject to any disclaimer, the term of this patent is extended or adjusted under 35 U.S.C. 154(b) by 566 days.

(21) Appl. No.: 12/624,150

(22) Filed: Nov. 23, 2009

(65) Prior Publication Data
US 2010/0063749 A1 Mar. 11, 2010

Related U.S. Application Data

(63) Continuation-in-part of application No. 11/007,681, filed on Dec. 8, 2004, now abandoned.

(60) Provisional application No. 60/592,175, filed on Jul. 29, 2004.

(51) Int. Cl.
*G01R 27/28* (2006.01)

(52) U.S. Cl.
USPC .......................................... 702/117

(58) Field of Classification Search ............... 702/117; 73/23.2, 25.01, 716
See application file for complete search history.

(56) References Cited

U.S. PATENT DOCUMENTS

| | | | | |
|---|---|---|---|---|
| 5,428,985 A | * | 7/1995 | Kurtz et al. ............... | 73/25.01 |
| 5,708,190 A | * | 1/1998 | Seefeldt et al. ............ | 73/23.2 |
| 6,401,541 B1 | * | 6/2002 | Kurtz ....................... | 73/716 |

* cited by examiner

*Primary Examiner* — Jonathan C Teixeira Moffat
*Assistant Examiner* — Xiuquin Sun
(74) *Attorney, Agent, or Firm* — Troutman Sanders LLP; James E. Schutz; Jihan A.R. Jenkins

(57) ABSTRACT

A gas density transducer including: a piezoresistive bridge sensor operative to provide an output indicative of an applied pressure, a computing processor having multiple inputs and at least one output, with the output of the bridge sensor coupled to an input of the processor; a temperature sensor coupled to an input of the processor for providing at an output a signal indicative of a temperature of the bridge sensor, the output of the temperature sensor coupled to an input of the processor; and, at least one memory accessible by the processor and having stored therein: compensation coefficients for compensating the output of the bridge sensor for temperature variation; an algorithm for solving Van der Waal's equation; and, code for providing at an output of the processor a signal indicative of a gas density when the bridge is subjected to a gas containing environment.

13 Claims, 3 Drawing Sheets

GAS DENSITY TRANSDUCER WITH A MICROPROCESSOR EXECUTING AN ALGORITHM SOLVING VAN DER WAAL'S EQUATION

RELATED APPLICATIONS

This application is a continuation-in-part application claiming priority under 35 U.S.C. §120 to U.S. patent application Ser. No. 11/007,681, now abandoned, entitled "GAS DENSITY TRANSDUCER", filed 8 Dec. 2004, which claims priority of U.S. Provisional Patent Application Ser. No. 60/592,175, also entitled "GAS DENSITY TRANSDUCER", filed 29 Jul., 2004, the entire disclosures of which are hereby incorporated as if being set forth in their entirety herein.

FIELD OF INVENTION

The present invention generally relates to a transducer apparatus, and more particularly, to a transducer apparatus which utilizes a microprocessor to determine gas density.

BACKGROUND OF THE INVENTION

It is believed to be desirable to measure gas densities, which indicate the mass of the gas if the volume of the container is known or fixed. Such measurements of gas densities within a pressurized tank can be used to monitor for gas leaks. Also the mass of gas is important in other applications where the gas is consumed constantly, e.g. an oxygen tank used on flight applications. Conventional transducers are not capable of outputting a signal corresponding to a gas density. Instead, a conventional transducer may output a signal indicative of pressure and/or temperature. That temperature and pressure may be used by an external processor to determine gas density by solving for Van Der Waal's equation. Such external processors, however, could not be integrated into the transducer due to the physical and operational requirements necessary for a processor to solve Van der Waal's equation. Simply put, processors capable of solving Van der Waal's equation were too large and required too much power to be placed within a transducer. Consequently, conventional transducers are limited to outputting raw measured data that is ultimately used by a processor external to the transducer to determine gas density. Therefore, in order to determined gas density, as is necessary for monitoring gas leaks in a pressurized tank, a separate processor is necessary in addition to the transducer. The size, complexity, and cost of such systems are significant drawbacks. Clearly, there is a need for transducer with an integrated processor that is capable of outputting a signal indicative of gas density.

SUMMARY OF THE INVENTION

Embodiments of the invention are directed to a system, method, and computer program product, wherein a transducer outputs a signal indicative of gas density. An exemplary embodiment of the invention may be a gas density transducer comprising a piezoresistive bridge sensor operative to provide an output indicative of an applied pressure, a computing processor having multiple inputs and at least one output, with the output of the bridge sensor coupled to an input of the processor; a temperature sensor coupled to an input of the processor for providing at an output a signal indicative of a temperature of the bridge sensor, the output of the temperature sensor coupled to an input of the processor; and, at least one memory accessible by the processor and having stored therein: compensation coefficients for compensating the output of the bridge sensor for temperature variation; an algorithm for solving Van der Waal's equation; and, code for providing at an output of the processor a signal indicative of a gas density when the bridge is subjected to a gas containing environment.

DETAILED DESCRIPTION OF THE PREFERRED EMBODIMENTS

Figure 1:
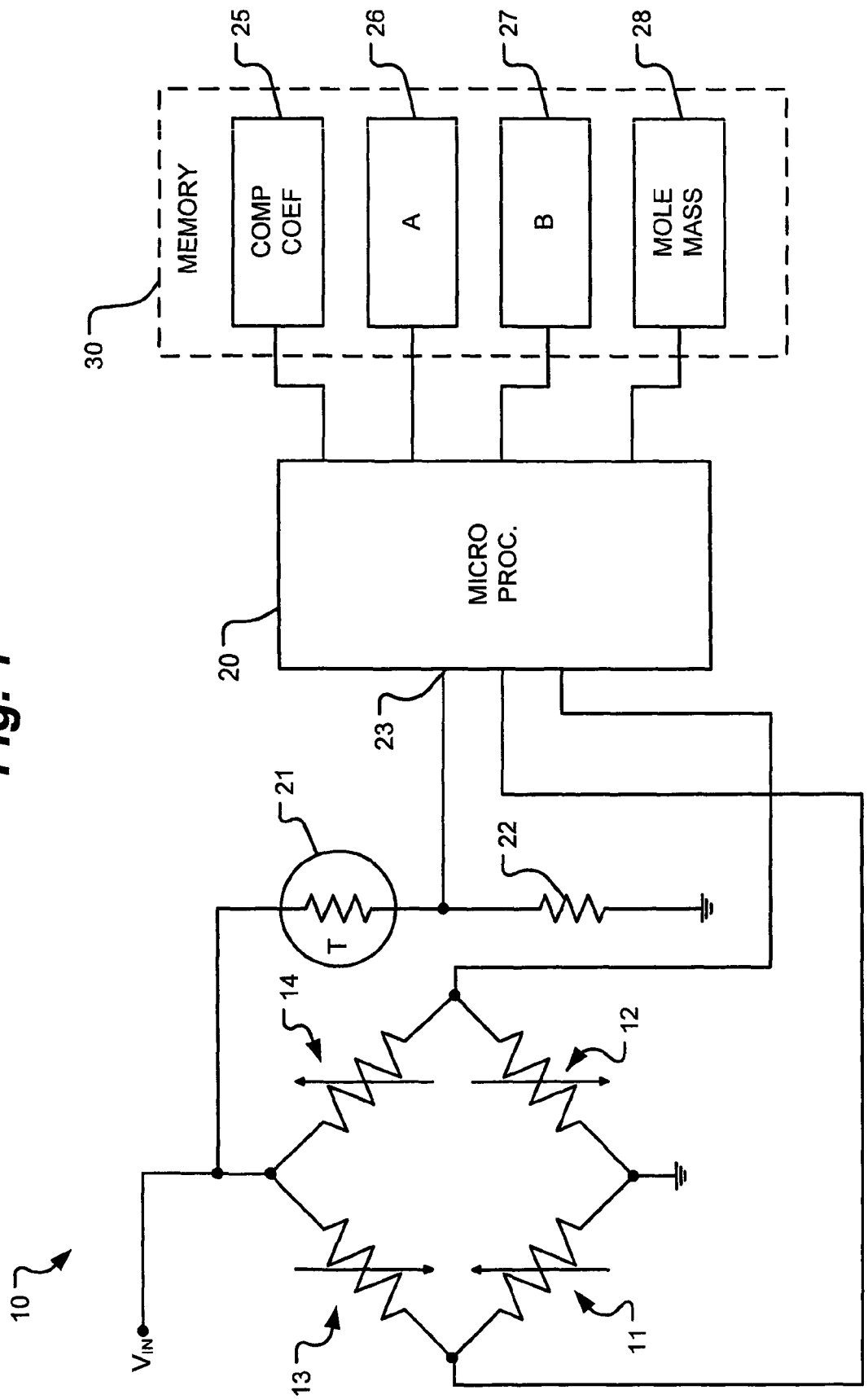
FIG. 1 illustrates a schematic diagram of a gas density transducer in accordance with an exemplary embodiment of the present invention

It is to be understood that the figures and descriptions of the present invention have been simplified to illustrate elements that are relevant for a clear understanding of the present invention, while eliminating, for purposes of clarity, many other elements found in typical transducer systems and methods of making and using the same. Those of ordinary skill in the art will recognize that other elements are desirable and/or required in order to implement the present invention. However, because such elements are well known in the art, and because they do not facilitate a better understanding of the present invention, a discussion of such elements is not provided herein.

According to an aspect of the present invention, where the gas volume is constant or known, a transducer output is indicative of the mass of the gas. This measurement is useful for determining the amount of gas in a container, where continuous gas consumption occurs and it is desirable to know the amount of gas remaining in a container, for example. This type of transducer has a distinct advantage over a standard pressure transducer, as the pressure can change due to temperature variations, for example.

Other applications of such transducers include the detection of leaks in a gas tank from where no consumption is supposed to occur during normal conditions. This, for example, can be an emergency oxygen tank or nitrogen pressure tank to be used in case of hydraulic failure. In such cases, simple pressure measurements may not be satisfactory, due at least in part to temperature effects.

In general, detecting gas leaks using the Van der Waal equation is well known. Reference is made to U.S. Pat. No. 5,428,985 entitled, "Gas Leak Detection Apparatus and Methods" issued on Jul. 4, 1995 to A. D. Kurtz et al. and assigned to Kulite Semiconductor Products, Inc., the assignee herein. This patent describes an improved gas leak detection apparatus for detecting a leak in a gas containing vessel of constant volume. The entire disclosure of U.S. Pat. No. 5,428,985 is hereby incorporated by reference as if being set forth in its entirety herein. The apparatus described therein compensates for deviations in the behavior of a contained gas from an ideal model. The apparatus incorporates a pressure transducer, an amplifier and feed back to effectively and accurately model the Van der Waal's equation for a given stored gas. The described apparatus is adaptable for operation with a number of different gases by changing circuit elements. The output of the apparatus is proportional to the total number of moles of gas present in the containment vessel at any particular time. As is well known, a mole equals $6*10^{23}$ molecules of a substance. This number of moles may be indicative of a leak from the vessel upon a realization that a reduction in the number of moles of the mass of the gas of the vessel has occurred (absent an intentional reduction).

The above-identified U.S. Pat. No. 5,428,985, along with U.S. Pat. No. 4,766,763 entitled, "Gas Leak Detection Apparatus and Methods" issued to A. D. Kurtz on Aug. 30, 1988, further indicate problems and drawbacks of devices that operate according to the ideal gas law. The entire disclosure of U.S. Pat. No. 4,766,763 is also hereby incorporated by reference as if being set forth in its entirety herein.

In an exemplary embodiment of the present invention, a gas density transducer utilizing a pressure transducer in conjunction with and under the control of an internal microprocessor, which executes an algorithm to solve Van der Waal's equation to provide reliable and accurate output indicative of gas density is disclosed.

In an exemplary embodiment, a gas density transducer measures the pressure and temperature of the gas, and using these parameters a microprocessor of the transducer executes an algorithm for solving Van der Waal's equation to calculate the gas density. The algorithm may be stored in a memory associated with the transducer. The memory may be internal or external to the transducer. As used herein, "memory" refers to one or more devices capable of storing data, such as in the form of chips, tapes or disks. Memory may take the form of one or more random-access memory (RAM), read-only memory (ROM), programmable read-only memory (PROM), erasable programmable read-only memory (EPROM), flash, or electrically erasable programmable read-only memory (EEPROM) chips, by way of further non-limiting example only.

Gas density can be calculated using the Ideal Gas Equation:

$$pV = nRT,\quad\quad\quad\quad\text{[Equation 1]}$$

where: p=pressure, T=absolute pressure, n=number of moles, V=volume, R=perfect gas constant. By measuring p and T, and knowing R, the gas density may be calculated in terms of moles/liter using the equation:

$$\frac{n}{v} = \frac{1}{R}*\frac{p}{T},\quad\quad\quad\quad\text{[Equation 2]}$$

where n/V is the gas density, in moles/liter.

This relation may be well suited for low gas densities, i.e., low pressures, up to about 300 pounds per square inch absolute (psia). Above this pressure, using this equation may produce significant errors.

For higher pressures and high gas densities, the same gas density n/V in moles/liters can be calculated using the Van der Waal's equation:

$$\left(p + a*\frac{n^2}{V^2}\right)(V - bn) = nRT,\quad\quad\quad\quad\text{[Equation 3]}$$

where a and b are known gas specific coefficients. These coefficients provide for corrections due to the non-zero volume of the molecules of gas b and the inter-molecular forces a. The Van der Waal's equation is a widely used formula, universally accepted, and consistently verified by experimental measurements. A major advantage of the Van der Waal's formula versus the Ideal Gas Equation is that it maintains its validity and accuracy over a wider range of pressures and temperatures.

By dividing both sides of the Van der Waal's equation by V one may obtain:

$$\left(p + a*\frac{n^2}{V^2}\right)\left(1 - b*\frac{n}{V}\right) = \frac{n}{V}*RT.\quad\quad\quad\quad\text{[Equation 4]}$$

Equation 4 above can be further simplified by introducing z, where z=n/V:

$$(p + a*z^2)(1 - b*z) = zRT.\quad\quad\quad\quad\text{[Equation 5]}$$

As discussed above, in Equation 5, pressure p and temperature T may be values known through measurement, and R is the Gas Constant (8.314 J·K$^{-1}$ mol$^{-1}$ in SI units). Additionally, a and b may also be known coefficients for the particular gas being measured.

In accordance with an exemplary embodiment of the invention, a microprocessor of the gas density transducer may determine the gas density z by executing an algorithm. The algorithm may provide variables $z_1$ and $z_2$, having initial values $z_1=0$ and $z_2=1/b$. The algorit may also provide a variable $z_n$, and define $z_n$ as:

$$z_n = \frac{z_1 + z_2}{2}.\quad\quad\quad\quad\text{[Equation 6]}$$

The algorithm may then substitute $z_n$, as defined in Equation 6 above, for z in Equation 5 and calculate a value for F:

$$F = (p + a*z_n^2)(1 - b*z_n) - z_nRT.\quad\quad\quad\quad\text{[Equation 7]}$$

If the value of F determined by solving Equation 7 using $z_n$ is greater than zero, then $z_n$ may be assigned as a new value for $z_1$. If the value of F determined by solving Equation 7 using $z_n$ is less than zero, then $z_n$ may be assigned as a new value for $z_2$. The algorithm may then calculate a new value for $z_n$ using the new value of $z_1$ or $z_2$ in order to calculate a new value for F using Equation 7. The algorithm is recursive and continues calculating new values for F based upon new values of $z_n$, which are in turn calculated based on new values of $z_1$ or $z_2$, depending upon the value of F, until:

$$|z_1 - z_2| < \frac{1}{b}*\frac{1}{2^x}.\quad\quad\quad\quad\text{[Equation 8]}$$

The resolution of this algorithm is determined by the value of x in $\frac{1}{2^x}$. In a preferred embodiment, the resolution is 16 bits, hence the value of x is 16. In other contemplated embodiments, that the resolution of the algorithm may be different and depend upon the capabilities of the processor and/or degree of accuracy desired.

Once the absolute value of $z_1$-$z_2$, is below $1/b*\frac{1}{2^x}$, a value for gas density can be output using from the following series of equations:

$$\frac{z_1 + z_2}{2} = z_n = z = \frac{n}{V}.\quad\quad\quad\quad\text{[Equation 9]}$$

This algorithm has the advantage that it performs only basic arithmetic operations (i.e., addition, subtraction, and multiplication), without the need for more complex operations such as division or square roots. The algorithm is very rapidly convergent. The rapid convergence and use of simple operations allow the algorithm to be executed by a small processor with limited operational capabilities. Such a processor may be substantially smaller in physical size and power consumption than the processors conventionally used to solve Van der Waal's equation. This reduction in size and power consumption allows for the microprocessor 20 to be integrated into the transducer 10. As a result, the overall size and number of components necessary for a system that determines gas density is reduced since the transducer 10 itself may output a signal indicative of gas density.

Referring now to FIG. 1, there is shown a schematic diagram of a pressure transducer 10 having a bridge configuration having piezoresistive elements 11, 12, 13 and 14 arranged in a Wheatstone Bridge configuration. In other contemplated embodiments, elements 11, 12, 13, and 14 may be replaced by another suitable pressure sensor. The output of the piezoresistive bridge configuration, or bridge, is directed to the inputs of a microprocessor 20, which operates to process the bridge signal to produce an output indicative of gas density. The microprocessor comprises circuitry to amplify the signals from the pressure and temperature sensors and to digitize these signals. There is also shown a temperature sensor 21. In an exemplary configuration, sensor 21 may take the form of temperature dependent resistive device, like a resistance temperature detector (RTD). For non-limiting purposes of further explanation only, RTDs use metals whose resistance increases with temperature. The resistivity of sensor 21 may increase linearly with temperature over a given range, and be related to the dimensions of the metal element thereof, such as length and cross-sectional area. According to an aspect of the present invention, sensor 21 may take the form of a semiconductor sensor or any other well known device which is responsive to temperature as well.

Referring still to FIG. 1, temperature sensor 21 is coupled in series with a resistor 22 between bridge input VIN and ground, with a terminal junction between the sensor 21 and resistor 22 also directed to an input 23 of the microprocessor 20. Input 23 may be a real-time, or substantially real-time input. Therefore, the microprocessor 20 receives an input, such as a voltage, indicative of temperature and also an input indicative of pressure.

In one configuration, the bridge and temperature sensors may both be positioned or mounted in or on a container, tank or other environment, where the gas density is to be monitored.

According to an aspect of the present invention, microprocessor 20 may include memory 30 that stores composition coefficients in a memory portion 25. These coefficients may be used to correct pressure readings due to the effects of temperature. Memory 30 may also store a and b coefficients in the memory portions 26 and 27, indicative of the coefficients specific to a particular gas, as indicated above for Van der Waal's equation. Memory 30 may also store, in a portion 28, values indicative of the molecular mass of the specific gas. Alternatively, memory 30, or one or more portions thereof, may be external to, but accessible by processor 20.

Figure 2:
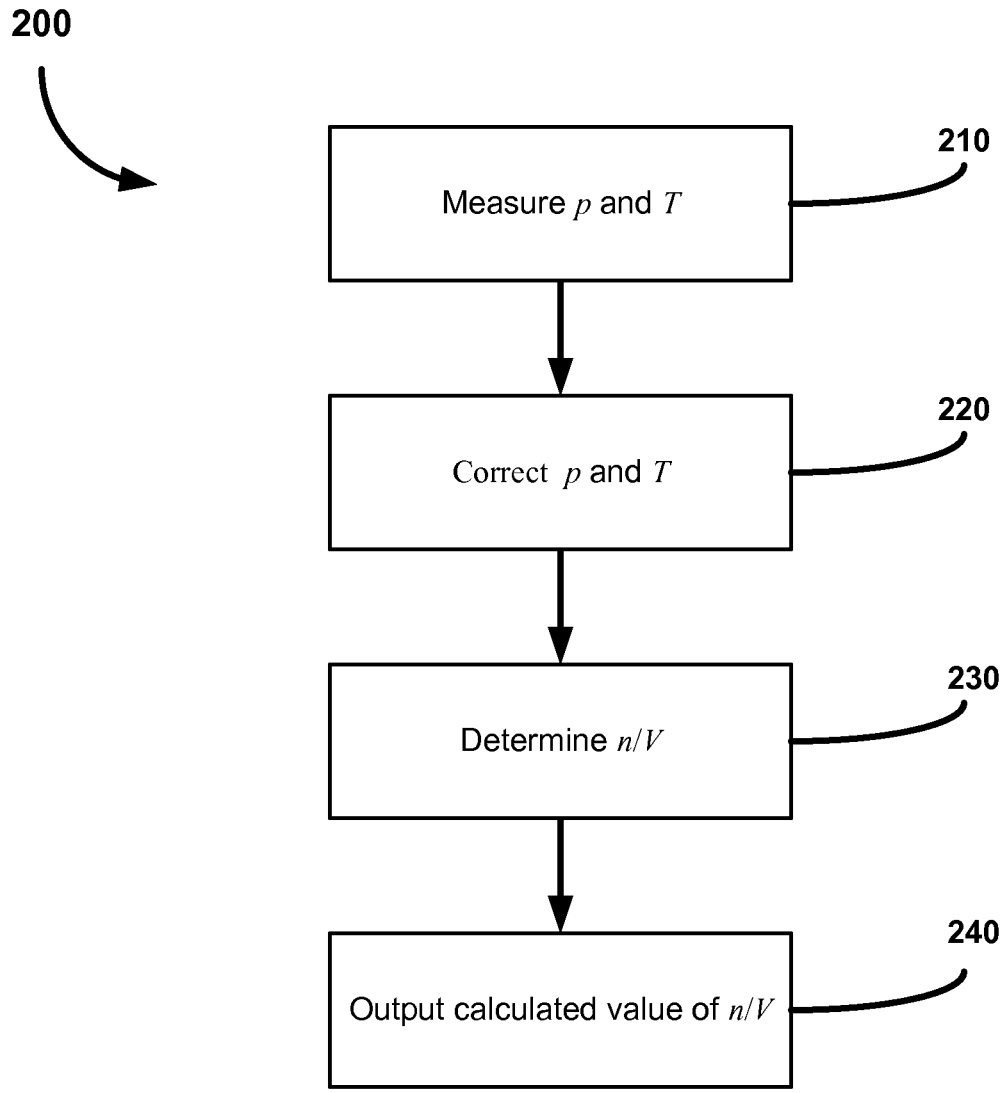
FIG. 2 illustrates a block diagram of a process suitable for use with the transducer of FIG. 1 in accordance with an exemplary embodiment of the present invention.

Referring now also to FIG. 2, there is shown a block diagrammatic representation of a process 200 being suitable for use with the transducer of FIG. 1. Process 200 may be executed in conjunction with or by microprocessor 20 using memory 30. A measurement of the raw output of the pressure sensor bridge 10 and the temperature sensor 21 may be taken at 210. Optionally, the bridge itself may take the form of a temperature compensated bridge, such as that shown in U.S. Pat. No. 6,700,473, entitled "PRESSURE TRANSDUCER EMPLOYING ON-CHIP RESISTOR COMPENSATION", or U.S. Pat. No. 5,686,826, entitled "AMBIENT TEMPERATURE COMPENSATION FOR SEMICONDUCTOR TRANSDUCER STRUCTURES", the entire disclosures of which are each also hereby incorporated by reference as if being set forth in their respective entireties herein. For example, bridge 10 may include one or more span-temperature compensating resistors. The temperature of the pressure sensor bridge may then be determined by measuring the resistance of the bridge, or span resistor, which changes in a predictable way with temperature. By measuring the resistance, the temperature that the bridge is subject to may be derivable by microprocessor 20.

According to an aspect of the present invention, the pressure and temperature data acquired from bridge 10 at 210 may be corrected at 220. Microprocessor 20 may correct the raw measurements to determine the pressure and temperature of the bridge with good accuracy. By way of non-limiting example, the correction may be based on the measured resistance of the bridge or span-temperature compensating resistor, and/or the output of RTD 21, using compensation coefficients stored in the memory portion 25 and a polynomial interpolation algorithm. These coefficients may be determined by individually testing the transducer for a wide range of temperatures and pressures. The determined correction coefficients may be stored in memory 25, for retrieval by microprocessor 20 during correction at 220. Thus, the determined bridge temperature may be correlated with correction coefficients stored in memory 30, which correlated coefficients may then utilized to correct the transducer output.

The gas density (n/V) may then be determined at 230 using a derived version of Van der Waal's equation provided above as Equation 5. The coefficients a and b, necessary for solving Equation 5, as well as the molecular mass of the gas, necessary for determining density, may be retrieved from memory portions 26, 27 and 28 by microprocessor 20.

Microprocessor 20 may solve Equation 5 for z by executing an algorithm. The algorithm may estimate an initial value z, whereby this value changes until a best approximation is reached. Such a method may be well suited for the Van der Waal equation, which is a third order type with no simple and explicit solution. An analog and/or digital output may then be provided at 240 by microprocessor 20 based on the solution reached at 230.

Figure 3:
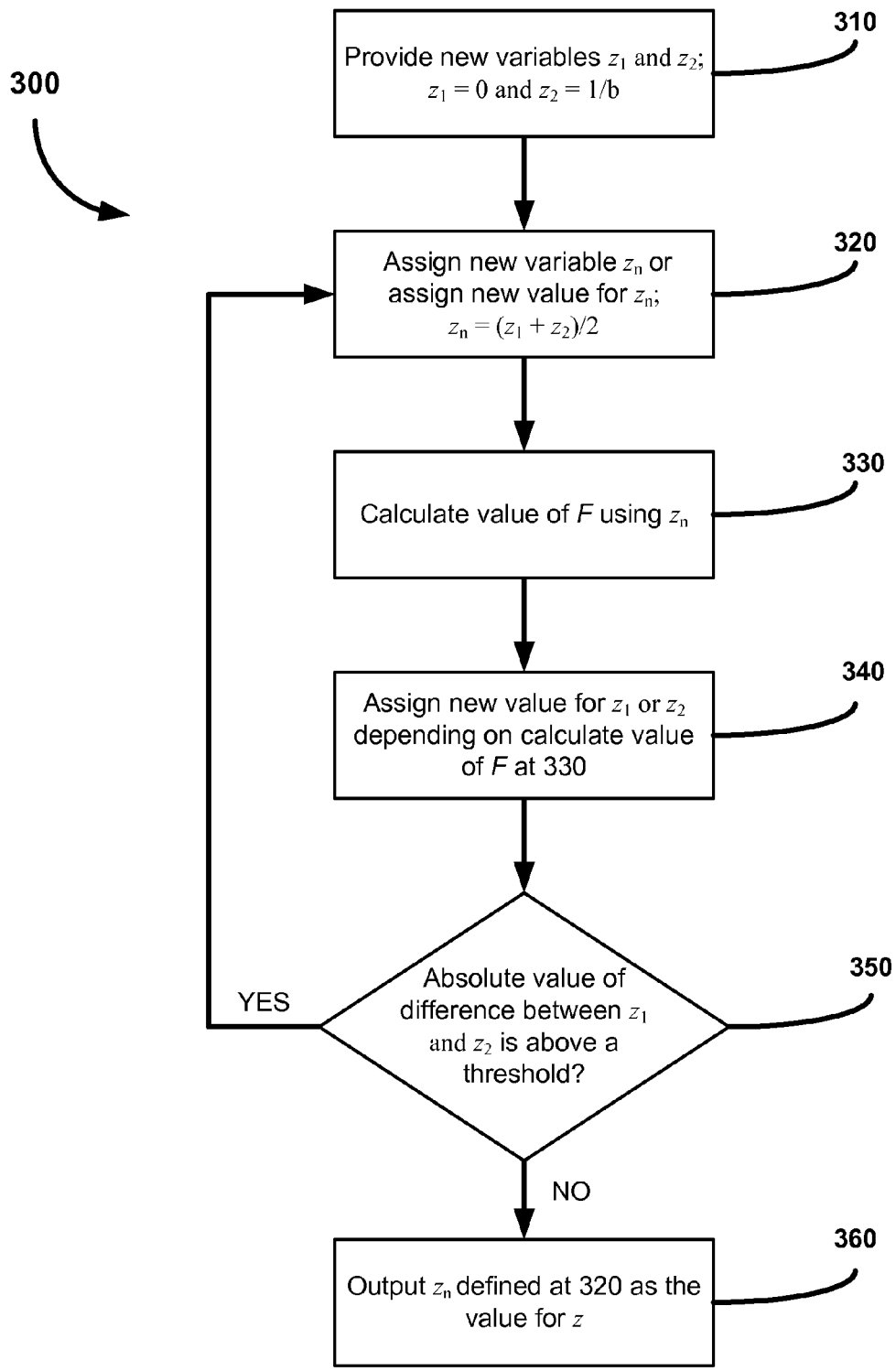
FIG. 3 illustrates a block diagram illustrating steps of an algorithm executed by a processor of the transducer of FIG. 1 in accordance with an exemplary embodiment of the present invention.

FIG. 3 illustrates a block diagram illustrating steps of an algorithm 300 executed by microprocessor 20 of the transducer 10 in accordance with an exemplary embodiment of the present invention. The algorithm 300 may be used for the determination of gas density (n/V) at 230 in process 200 of FIG. 2. The algorithm may solve Equation 5 above to provide an approximate value for z, which is equal to the gas density n/V. Since n/V is density in moles/liter, the microprocessor 20 may determine density in grams/liter by multiplying by the molecular mass stored in a memory portion 26.

The algorithm 300 may provide two new variables $z_1$ and $z_2$, and define $z_1=0$ and $z_2=1/b$ at 310. The algorithm 300 may also provide a new variable $z_n$ at 320, where $z_n=(z_1+z_2)/2$. At 330, the algorithm 300 may calculate a value for F in Equation 7 using $z_n$. The algorithm may next assign new values for $z_1$ or $z_2$ at 340 based upon the calculated value of F at 330. If the value of F at 330 is greater than zero, then $z_n$ may be the new assigned value for $z_1$. If the value of F at 330 is less than zero, then $z_n$ may be the new assigned value for $z_2$. At 350, the algorithm may determine the absolute value of the difference between $z_1$ and $z_2$. If the absolute value of the difference is greater than or equal to $1/b*1/65536$, then the algorithm may repeat steps 320 through 350: assigning a new value for $z_n$; calculating a new value for F; assigning new values for $z_1$ or $z_2$; and determining whether the new values of $z_1$ or $z_2$ satisfy resolution threshold. If the absolute value of the difference is less than $1/b*1/65536$, then at 360 the algorithm 300 may output the new value of $z_n$ assigned at 320 as the best approximate value of z, and hence n/V. A value other than 1/65,536 may be used at 350 depending upon the bits of resolution desired and/or processor being used, as explained above. The processor 20 may then use the molecular mass stored in a memory portion 26 to calculate the density of the gas.

The memory 30 may comprise a program stored on a computer readable medium for executing the algorithm 300. In accordance with an exemplary embodiment of the invention, the computer readable program for executing the algorithm 300 is provided in the Appendix to the Specification of U.S. Provisional Patent Application Ser. No. 60/592,175. The program is in source code and embodies an aspect of the present invention. The computer program code is loaded into and executed by a processor such as microprocessor 20, or may be referenced by a processor that is otherwise programmed, so as to constrain operations of the processor and/or other peripheral elements that cooperate with the processor. When such programming is executed by a suitable computing device, such as microprocessor 20, the processor or computer becomes an apparatus that practices an embodiment of a method of the present invention. When so implemented on a general-purpose processor, the computer program code segments configure the processor to virtually create specific logic circuits. Variations in the nature of the program carrying medium, and in the different configurations by which computational and control and switching elements can be coupled operationally, are all within the scope of the present invention disclosed herein.

The algorithm 300 described above, can determine the gas density with good accuracy. For oxygen and nitrogen, and for pressures up to 5000 psia, and for a temperature range between −55° C. and +125° C., the accuracy of the gas density measurement may be better than ±0.25% of full scale. Such accuracy may be due at least in part to good pressure and temperature measurements, ±0.1% of full scale for pressure and ±0.5° C. for temperature.

According to an aspect of the present invention, such a transducer 10 output may be indicative of the time left for usage of a gas tank based on the determined quantity of gas and a known consumption rate. Alternatively, given that V is constant, changes in density may also be indicative of a leak in a container. Such calculations may be performed by microprocessor 20 or other computational device(s) using conventional methodologies.

It will be apparent to those skilled in the art that various modifications and variations may be made in the apparatus and process of the present invention without departing from the spirit or scope of the invention. Thus, it is intended that the present invention cover the modification and variations of this invention provided they come within the scope of the appended claims and their equivalents.

The invention claimed is:

1. A gas density transducer comprising:
a pressure sensor providing an output indicative of a pressure applied by a sample gas;
a temperature sensor providing an output indicative of a temperature of the sample gas; and
a microprocessor having an output, a first input coupled to the output of the pressure sensor, and a second input coupled to the output of the temperature sensor, the microprocessor providing an output indicative of the density of the sample gas,
the microprocessor configured to determine a value for z in the equation $(p+a*z^2)(1-b*z)=zRT$, wherein $z=n/v$ and
1) provide new variables $z_1$ and $z_2$, and define $z_1=0$ and $z_2=1/b$;
2) assign new variable $z_n$, wherein $z_n=(z_1+z_2)/2$;
3) substitute $z_n$ for z in $(p+a*z^2)(1-b*z)=zRT$, and calculate value of F in $F=(p+a*z_n^2)(1-b*z_n)-z_nRT$;
4) assign new values for $z_1$ or $z_2$, wherein a new value for $z_1$ is $z_n$ defined in step 2 if the value of F calculated in step 3 is greater than zero, and a new value for $z_2$ is $z_n$ defined in step 2 if the value of F calculated in step 3 is less than zero;
5) repeat steps 2-4 if the absolute value of the difference between $z_1$ and $z_2$ is greater than $1/b*\frac{1}{2}^x$, wherein x is a predetermined number of bits of resolution; and
6) output $z_n$ calculated in step 3 as the approximate value of n/V if the absolute value of the difference between $z_1$ and $z_2$ is less than $1/b*\frac{1}{2}^x$.

2. The transducer of claim 1, the microprocessor configured to calculate the density of the sample gas from a known molecular mass of the sample gas and $z_n$ output in step 6.

3. The transducer of claim 2 further comprising, a memory accessible by the processor, the memory having stored therein:
compensation coefficients for correcting the outputs of the pressure and temperature sensors;
gas specific coefficients a and b for the Van der Waal's equation;
the molecular mass of the sample gas; and
an algorithm executable to perform steps 1-6.

4. The transducer of claim 1, wherein the temperature sensor is a resistance temperature detector (RTD).

5. The transducer of claim 1, wherein the pressure sensor is a piezoresistive bridge.

6. The transducer of claim 1, wherein the pressure sensor and temperature sensor are co-excited by the same sample gas.

7. A method for using a gas density transducer to determine the density of a sample gas, the method comprising:
measuring pressure applied by a sample gas using a pressure sensor;
measuring temperature of the sample gas using a temperature sensor; and
calculating the density of the sample gas using a microprocessor having a first input coupled to an output of the pressure sensor, a second input coupled to an output of the temperature sensor, and an output providing a signal indicative of the density of the sample gas;
calculating the density of the sample gas comprising determining a value for z in the equation $(p+a*z^2)(1-b*z)=zRT$, wherein $z=n/V$, by
1) providing new variables $z_1$ and $z_2$, and define $z_1=0$ and $z_2=1/b$;
2) assigning new variable $z_n$, wherein $z_n=(z_1+z_2)/2$;
3) substituting $z_n$ for z in $(p+a*z^2)(1-b*z)=zRT$, and calculating value of F in $F=(p+a*z_n^2)(1-b*z_n)-z_nRT$;
4) assigning new values for $z_1$ or $z_2$, wherein a new value for $z_1$ is $z_n$ defined in step 2 if the value of F calculated in step 3 is greater than zero, and a new value for $z_2$ is $z_n$ defined in step 2 if the value of F calculated in step 3 is less than zero;

5) repeating steps 2-4 if the absolute value of the difference between $z_1$ and $z_2$ is greater than to $1/b*\frac{1}{2}^x$, wherein x is a predetermined number of bits of resolution; and 6) output $z_n$ calculated in step 3 as the approximate value of n/V if the absolute value of the difference between $z_1$ and $z_2$ is less than $1/b*\frac{1}{2}^x$.

8. The method of claim 7 further comprising, calculating the density of the sample gas from a known molecular mass of the gas and $z_n$ output in step 6.

9. The method of claim 8 further comprising, storing in a memory:

compensation coefficients for correcting the outputs of the pressure and temperature sensors;

gas specific coefficients a and b for the Van der Waal's equation;

the molecular mass of the sample gas; and an algorithm executable to perform steps 1-6.

10. The method of claim 7, wherein steps 1-6 are performed by a microprocessor of the gas density transducer executing an algorithm.

11. The method of claim 7 further comprising, correcting the measured pressure and temperature using compensation coefficients prior to determining a value for z.

12. The method of claim 7, wherein the arithmetic functions employed by the microprocessor to perform steps 1-6 consist of addition, subtraction, and multiplication.

13. A computer program product stored on a non-transitory computer readable medium, the program product executable to perform a method comprising:

receiving a pressure signal indicative of a pressure of a sample gas;

receiving a temperature signal indicative of a temperature of the sample gas;

determining a value for z in the equation $(p+a*z^2)(1-b*z)=zRT$, wherein z=n/V, p is the pressure provided by the received pressure signal, and T is the temperature provided by the received temperature signal, by performing the following:

1) providing new variables $z_1$ and $z_2$, and define $z_1=0$ and $z_2=1/b$;

2) assigning new variable $z_n$, wherein $z_n=(z_1+z_2)/2$;

3) substituting $z_n$ for z in $(p+a*z^2)(1-b*z)=zRT$, and calculating value of F in $F=(p+a*z_n^2)(1-b*z_n)-z_nRT$;

4) assigning new values for $z_1$ or $z_2$, wherein a new value for $z_1$ is $z_n$ defined in step 2 if the value of F calculated in step 3 is greater than zero, and a new value for $z_2$ is $z_n$ defined in step 2 if the value of F calculated in step 3 is less than zero;

5) repeating steps 2-4 if the absolute value of the difference between $z_1$ and $z_2$ is greater than $1/b*\frac{1}{2}^x$, wherein x is a predetermined number of bits of resolution; and 6) output $z_n$ calculated in step 3 as the approximate value of n/V if the absolute value of the difference between $z_1$ and $z_2$ is less than $1/b*\frac{1}{2}^x$; and calculating the density of the sample gas from a known molecular mass of the gas and $z_n$ output in step 6.

* * * * *